United States Patent [19]

Erdt et al.

[11] Patent Number: 4,726,936
[45] Date of Patent: Feb. 23, 1988

[54] APPARATUS FOR INJECTING A SUBSTANCE INTO A REACTION VESSEL

[75] Inventors: Kurt Erdt, Wesseling; Albert Merz, Karlsruhe; Günter Ritter, Brühl, all of Fed. Rep. of Germany

[73] Assignees: Rheinische Braunkohlenwerke AG.; Kernforschungszentrum Karlsrume GmbH, both of Fed. Rep. of Germany

[21] Appl. No.: 677,779

[22] Filed: Dec. 4, 1984

[30] Foreign Application Priority Data

Dec. 10, 1983 [DE] Fed. Rep. of Germany ....... 3344789

[51] Int. Cl.[4] .............................. B01J 3/02; C21C 4/06
[52] U.S. Cl. ................................... 422/159; 422/903; 222/389
[58] Field of Search ................ 422/159, 903; 222/389; 137/268

[56] References Cited

U.S. PATENT DOCUMENTS

| | | | |
|---|---|---|---|
| 1,314,468 | 8/1919 | Dunbar | 222/389 |
| 2,891,622 | 6/1959 | Patterson et al. | 137/268 |
| 3,399,676 | 9/1968 | McLaughlin | 137/268 |
| 3,883,431 | 5/1975 | Ishii et al. | 137/268 |
| 4,441,629 | 4/1984 | Mackal | 222/389 |
| 4,513,767 | 4/1985 | Soederhoyzen | 137/268 |

FOREIGN PATENT DOCUMENTS

| | | | |
|---|---|---|---|
| 631313 | 8/1963 | Belgium | 422/159 |
| 2257669 | 11/1972 | Fed. Rep. of Germany. | |

Primary Examiner—David L. Lacey
Attorney, Agent, or Firm—Panitch Schwarze Jacobs and Nadel

[57] ABSTRACT

In a process for injecting a radioactive sample of a substance into a reaction vessel, the sample is first enclosed in a first container in which it is irradiated, and then the first container with sample is placed in a second container which is separated from the reaction vessel by way of a closed valve. The second container is heated, and the sample is then conveyed out of the containers into the reaction vessel through the valve which is opened. The sample is enclosed within the first container by plugs or is frozen therein for which purpose the first container may possibly by put into intermediate storage in a storage container. An apparatus comprises the first container for receiving the sample, to be arranged and fixed within the second heatable pressure-resistant container which can be communicated with the reaction vessel through a valve.

6 Claims, 3 Drawing Figures

APPARATUS FOR INJECTING A SUBSTANCE INTO A REACTION VESSEL

BACKGROUND OF THE INVENTION

The invention relates to a process and an apparatus for injecting a radioactive sample of a substance into the reaction chamber of a reaction vessel for conversion of said substance, using an injection medium.

Faced with the looming worldwide shortage of crude oil, there has been an increasing trend in recent times to turn development towards the conversion of solid fossil fuels into high-energy liquid products. Most hard coals and brown coals or lignites for example are suitable for hydrogenating liquefaction. However, the pressures and temperatures required for carrying out the conversion operation are unusually high in comparison with other technical processes. Accordingly, high levels of requirement are made in regard to the structure of the reaction vessels and the mode of carrying such a process into effect. In connection with the way in which the process is carried out, it is important for example to establish the residence time of the coal to be converted in the reaction vessel, and thus the rate of throughput. A suitable way of doing that is measuring by means of radioactive substances which are introduced into the reaction vessel in order to ascertain the residence time thereof by means of counter tubes. However, when dealing with high-pressure and high-temperature reaction vessels, difficulties are encountered in regard to introducing radioactive trace substances of that kind into the reaction vessel and the reaction procedure which takes place therein and which, in the case of a hydrogenating liquefaction operation, is carried out under pressures of the order of magnitude of from 300 to 500 bars and at temperatures of the order of magnitude of from 700° to 800° C.

The idea of injecting substances into apparatuses or plants which are not under an increased pressure, by means of injection devices, for example simple injection nozzles, has long been known. In that procedure, the substances to be injected are disposed in a closed container comprising for example glass, which is inserted into and enclosed in the injection device and which is then crushed to liberate the substance to be injected, within the injection device. However, in that operation, difficulties may occur as glass splinters which are produced as a result of crushing the glass container can pass into the injection passage and can cause stoppages therein. Difficulties of that nature mean that it is not always possible to obtain precise measurement values. It will be appreciated that the known methods are out of the question from the outset, when the reaction vessels involve high pressures and high temperatures, as, when discharging the substances forming the result of the conversion operation from the reaction zone, and with the relief of pressure which occurs when that operation is performed, the energy conversion phenomena that occur, for example pressure is converted into flow energy or kinetic energy, are such that the valves and other equipment at the corresponding locations involved in that operation tend to be damaged or ruined by foreign bodies which may possibly be contained in the conversion substance. In any case, because of the operating conditions involved, the discharge members on the reaction vessels have a comparatively short operating life, even though they are made from high-grade materials, and renewing them is expensive. It would be prohibitive for the service life that can be achieved to be reduced due to influences as indicated above.

SUMMARY OF THE INVENTION

An object of the present invention is to provide a process for injecting a radioactive sample of a substance into the highly pressurized interior of a reaction vessel in which a substance is undergoing conversion.

Another object of the invention is to provide a process for injecting a radioactive sample of a substance into the pressurized interior of a reaction vessel wherein the substance is undergoing conversion, which does not involve major difficulty in regard to handling the radioactively irradiated sample.

Still another object of the present invention is to provide a process for injecting a radioactive sample of a substance into a pressurised reaction vessel, which permits a precisely controlled quantity of the sample to be readily injected.

Yet another object of the present invention is to provide such a process which enables the sample which is to be injected, to be radioactively irradiated without serious difficulty.

A further object of the present invention is to provide an apparatus for injecting a radioactive sample of a substance into a reaction chamber, which permits a precisely controlled quantity of the substance to be disposed in a readily handleable container within which it can be radioactively irradiated without difficulty and subsequently injected.

A still further object of the present invention is to provide such an apparatus which is durable and reliable in operation.

These and other objects are achieved by means of a process for injecting a radioactive sample of a substance into the reaction chamber of a reaction vessel for conversion of said substance using an injection medium. The sample is irradiated within a first container and, together therewith, is enclosed in a second container which can be separated from the pressurized interior of the reaction chamber, as by means of a valve. The second container with the irradiated sample therein is then optionally heated, and the sample is conveyed out of the first and second containers into the reaction chamber, by opening of the valve, by means of an injection medium which is under a pressure higher than the internal pressure in the reaction chamber.

Apparatus for carrying out the process in accordance with the principles of the invention comprises a first container for receiving the sample to be irradiated therein, and a second pressure-resistant container which may be adapted to be heated when the first container with the sample therein, has been disposed in the second container. The second container can then be connected to the reaction vessel into which it is to be injected, by way of a suitable closure or shutoff means. The second container further has an intake opening for the injection medium to be introduced thereinto, thereby to discharge the irradiated sample from the second container into the reaction chamber.

It will be seen therefore that a radioactive sample of a substance can be introduced into the interior of a reaction vessel in which that or another substance is undergoing conversion under high pressure and at elevated temperature. The process and the apparatus are simple and straightforward in regard to the manner of performance of the process and the apparatus configuration.

As will be more clearly apparent hereinafter, an advantage of the mode of operation in accordance with the invention lies in good and easy handleability of the radioactively irradiated probe or sample, being first enclosed in a precisely controlled quantity in a manageable first container within which it can be radioactively irradiated. Then, the first container with the sample therein, now being radioactive, is put into a second container which is of a pressure-resistant and generally correspondingly thick-walled construction. The second container can then be connected to the high-pressure reaction vessel by way of a shut-off or closure member such as a valve, which is opened for the purpose of introducing the radioactive substance but which is otherwise closed.

Desirably, the radioactive sample employed is a substance which is the same as or of the same nature as that which is being converted within the reaction vessel. For example, when dealing with the hydrogenating liquefaction of coal, such a sample may comprise the same or similar finely ground coal or such a coal suspended in oil. The use of a sample which is adapted to the substance in the reaction vessel, in that way, ensures that conversion of the substance in the interior of the reaction vessel is not adversely affected, as the sample itself also takes part in the conversion operation. In addition, in that way, the conversion products are not affected by the sample.

A preferred mode of carrying the process into effect provides that the sample is enclosed within a first container which is of substantially cylindrical form and which has open ends. It may therefore be a tube portion, and the discharge opening thereof is advantageously slightly constricted. That means that the discharge flow speed of the sample is slightly increased so that it can be introduced into the reaction vessel without loss, through the injection opening and the valve when the latter is in an open condition.

The intake opening and the discharge opening of the first container can be closed off with plugs or stoppers of a suitable material such as wax in order to retain the sample within the first container. A closure arrangement of that kind is adequate to permit the sample to be safely and securely handled during the radioactive irradiation operation. When converting coal for example, when wax is is used for the stoppers or plugs, it does not cause contamination of the substances which are being converted within the reaction vessel. Another advantageous possibility provides using a sample in the form of a coal-oil suspension which is introduced into the first container and which is then frozen therein by subzero cooling. When in a frozen condition, such a sample can be easily handled and subjected to radioactive radiation, in order then to be introduced into the reaction vessel.

For the purposes of releasing the sample which is enclosed in or frozen in the first container, the second container can be heated, which causes the plugs or stoppers, or the sample itself, to melt after the first container has been introduced into the second container. By virtue of the second container being heated, the temperature and thus the viscosity of the sample can be accurately adjusted to the conditions of the conversion operation, which obtain in the reaction vessel, whereby it is possible to ensure that the reaction procedure within the reaction vessel is not detrimentally affected.

For the purposes of better handling of the sample during the radioactive irradiation step and also for complying with the safety provisions which are required in that respect, it has been found advantageous for the first container to be put into intermediate storage in a storage container from which it is removed after the irradiation operation and then introduced into the second container. The sample or the first container is usually handled with tools which are suited to that purpose, so that it is possible to avoid the activated components being directly touched by hand.

After the first container with the activated and possibly deep-frozen sample has been removed from the above-mentioned storage container and introduced into the second container, the first container is fixed within the second container, preferably by means of a clamping ring, and is sealed with respect to the second container in such a way that it is not subjected to the effect of a pressure from the exterior. There is therefore no possibility of the first container suffering deformation and being rendered useless, with the troublesome consequences that that would evolve, when the second container is subjected to a pressure. After the first container has been inserted and secured, the second container is closed with a high-pressure screw means which may preferably have a conical or tapered sealing edge which comes to bear against a co-operating surface of the second container in such a way that here too the necessary seal is formed. A construction of that kind has been found to be substantially more advantageous and reliable and also durable, than conventional sealing arrangements using ring seals or the like.

In accordance with a further preferred feature of the invention, the sample which is enclosed in the second container may be subjected to a preliminary pressure by way of the connection for the injection medium or agent, making use of the latter for that purpose. The injection agent is for example a fluid which corresonds to the fluid by means of which the substance in the reaction vessel is being converted, being therefore for example oil when converting coal. Between the sample to be injected and the high-pressure closure of the second container is a small internal space or cavity in which the preliminary pressure of the injection agent takes effect. That preliminary pressure is for example from 20 to 50 bars and causes the sample substantially to remain in its position within the first container, or at least not to change its position in the opposite direction to the direction of injection, when the plugs or stoppers are removed or when the frozen sample is made fluid, and before it is injected into the reaction vessel. The operations of fixing the first container within the second container, heating the sample and applying the preliminary pressure by way of the injection agent ensure that in each case the sample to be injected is in a condition in regard to pressure, temperature and viscosity in which it is best suited for the injection process and is adapted in the best possible manner to the conditions in the reaction vessel. Those conditions can be experimentally ascertained and established in detail beforehand.

DESCRIPTION OF THE PREFERRED EMBODIMENTS

Figure 1:
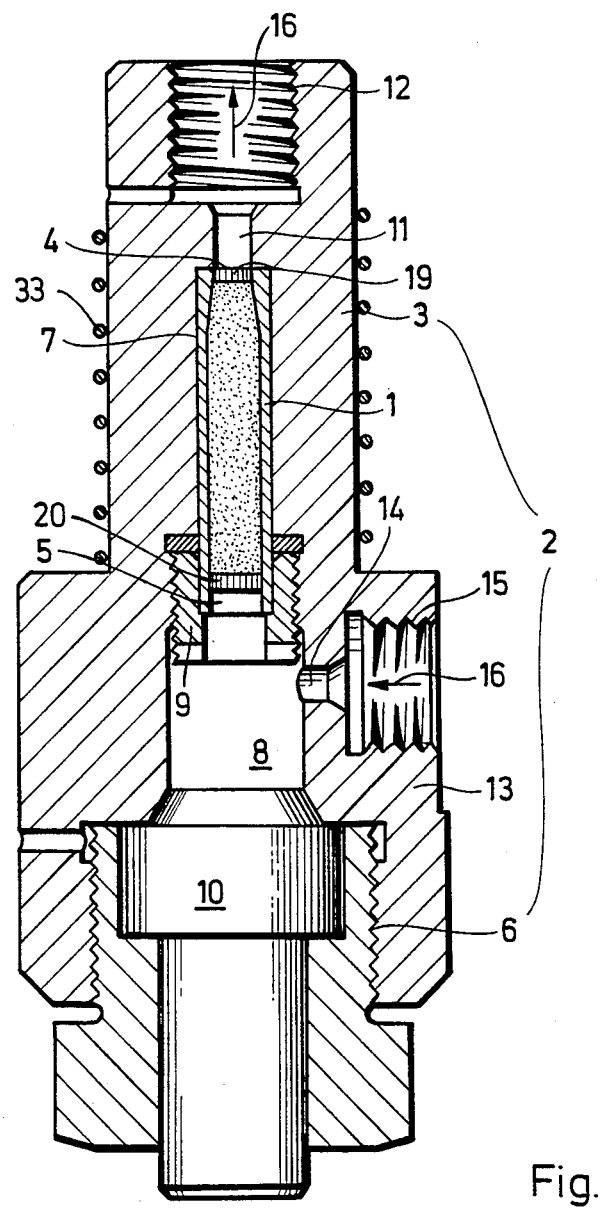
FIG. 1 is a view in longitudinal section through an apparatus for injecting a radioactive substance, with first container.

Referring to FIG. 1, it will be seen therefrom that in the operative condition of the apparatus, disposed in the upper or front portion 3 of a housing 2, representing a second container, of the injection apparatus, which can be heated as by an electrical heating means 33 is a sleeve member or tube 1 which represents a first container. The tube 1 is provided with a closable opening 4 and 5 at each end. The tube 1 is introduced into the housing 2 of the injection apparatus through a charging opening 6. In the illustrated position the tube 1 is carried in the upper or front portion 3 of the housing 2, or more precisely, the space 7 within same, with such an accurate fit therein that there cannot be any flow around the outside wall surface of the tube 1. The tube 1 is fixed in the space 7 by means of a clamping ring 9 which can be screwed in through the charging opening 6 while the latter is open. A space 8 inside the housing 2, below or rearwardly of the ring 9, is also accessible through the opening 6 which can be closed by means of a high-pressure closure arrangement 10. The discharge opening 4 of the tube 1 is aligned with an injection opening 11 for the discharge of sample and injection agent. From the discharge opening 4, a feed conduit leads by way of a highpressure screw connection 12 to the interior of the reaction vessel (not shown in FIG. 1 but shown at 25 in FIG. 3) which in operation is under a high pressure and at a high temperature.

Provided in a lower or rearward portion 13 of the housing 2, in the side wall thereof, is a flow opening or port 14 for the intake of the injection agent, the port 14 also being provided with a high pressure screw connection as indicated at 15 for connecting a feed conduit thereto. The port 14 communicates with the space 8 inside the housing 2, upstream of the tube 1 or the intake opening 5 thereof, as considered in the direction of flow of the injection agent as indicated at 16.

Figure 3:
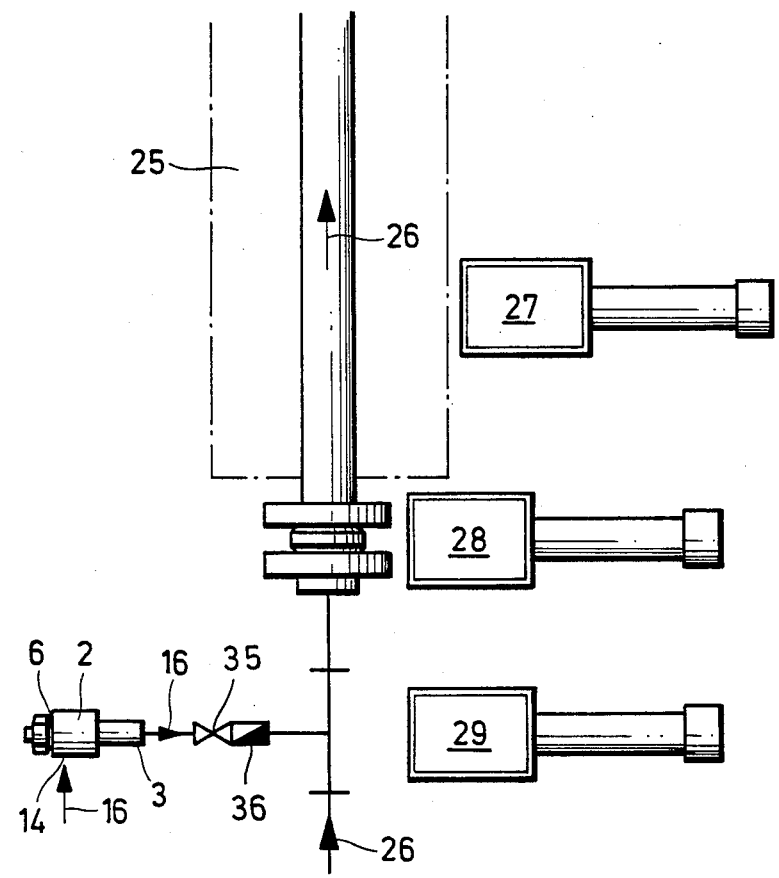
FIG. 3 is a diagrammatic view of the injection apparatus, in relation to a reaction vessel.

Referring also at this point to FIG. 3, disposed between the high-pressure screw connection 12 and the reaction vessel 25 are a high-pressure valve 35 and, possibly, in conjunction therewith, a check valve 36 which is temporarily opened for carrying out the injection operation. The injection apparatus can be fixedly connected to a container for the injection agent, for example oil when injecting coal, by way of the screw connection 15. The injection agent is essentially a conveyor agent or flow medium for the sample to be injected. The connection 15 also has a further valve (not shown) with which the container for the injection agent can be switched on and off as required.

Figure 2:
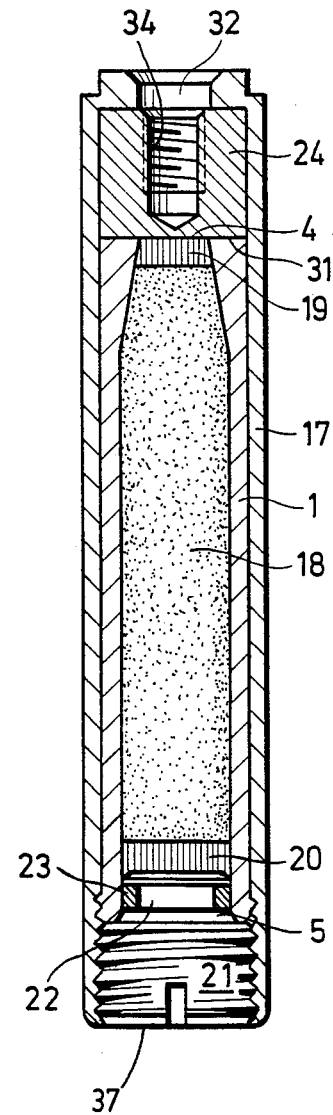
FIG. 2 is a view in longitudinal section through the first container which contains the sample and which is disposed in a storage container.

Referring to FIG. 2, shown therein on a larger scale is the sleeve member or tube 1 which is used for carrying out the radioactive irradiation operation and possibly freezing the sample, in a storage container 17. The tube 1 comprises a cylindrical metal tube which is slightly tapered inwardly at its upper end which has the discharge opening 4 to provide a constriction in the flow therethrough. The second or intake opening through which the injection agent passes into the tube 1 at the other end thereof is indicated at 5.

Shown within the tube 1 is a sample 18 to be injected. In a specific situation of use, the substance involved may be for example radioactively marked coal powder or a coal-oil suspension which is also marked. The openings 4 and 5 of the tube 1 are closed by closure plugs or stoppers 19 and 20 which can be easily melted and which comprise a suitable material for example wax. If the sample 18 is formed by a coaloil suspension, the plugs or stoppers 19, 20 may be omitted if the sample 18 has a sufficiently high solidification temperature.

The storage container 17 in which the tube 1 is put into intermediate storage after the sample 18 has been radioactively irradiated also comprises a metal tube and can be closed at its one end by a screw-in plug or stopper 21 which has a shoulder portion 22 and a seal 23, which project into the opening 5 of the tube 1 and in so doing seal it off. Disposed at the other end of the container 17, within the container, is a further plug or stopper 24 which has a screw-threaded bore 34 for connection to an ejector member, for example a rod or bar. The screw-threaded bore 34 is a blind bore so that a sealing action is produced between the plug or stopper 24 and the tube 1, in the region of the edge 37. The plug or stopper 24 is mounted movably in the storage container 17 so that, after the plug or stopper 21 has been removed, the tube 1 can be easily pushed out of the container 17 for unloading same, through the opening 31 of the container 17. It will be seen that the container 17 has an inwardly extending flange at its end adjacent the stopper 24 to hold the latter in the container 17.

The plug or stopper 24 can be braced with respect to the sleeve or tube 1, for sealing purposes. That can be effected in a simple manner by cooling, as is required in many situations in any case, as when using a coal-oil suspension as the sample. The severe cooling action results in shrinkage of the container 17 both in the peripheral direction and also in the longitudinal direction, the lengthwise shrinkage meaning that the plug or stopper 24 is pressed firmly against the end face of the sleeve member or tube 1, that has the discharge opening 4 therein.

FIG. 3 shows the injection apparatus in conjunction with a reaction vessel for converting a substance in a high-pressure process. The substance to be converted flows through the reaction vessel 25 in the direction indicated by the arrow 26. Beside the reaction vessel 25, there are measuring devices 27, 28 and 29 and possibly further measuring devices which are arranged in a distributed array along the longitudinal axis of the reaction vessel 25 and by means of which, after a radioactive substance has been injected, the path of movement thereof, the residence time and so forth in the product flow in the reaction vessel can be followed.

The kind and nature of substance to be injected generally depend on the nature of the phase in which the product flow to be investigated occurs. Depending on whether the product flow is in gaseous, liquid, possibly pasty or pulpy or solid form, the above-described apparatus can also be used for injecting gas, liquid or solid.

An embodiment of the process provides the following mode of operation, using the injection apparatus shown in FIG. 1 and the storage container 17:

1. Charging the tube 1 for the purposes of irradiation of the substance:

(a) Charging with coal powder:

The steps of: casting the closure plug or stopper 19 of a fusible material in the upper slightly conical portion of the tube 1, with subsequent setting of the plug or stopper; introducing coal powder into the tube 1; closing the tube 1 at the other lower end by means of a wax plug or stopper 20, with subsequent setting thereof, in which connection the plug 20 can be prevented from falling out by means of a groove formed in the tube member, thus providing a form-locking or positive securing action; introducing the tube 1 into the container 17; and closing same by means of the screw plug 21. It will be appreciated that the tube 1 can also be charged when it is already in the container 17.

(b) Charging with a coal-oil suspension:

The steps of: dropping the suspension when of high viscosity into the tube 1 which has been introduced into the storage container 17; closing the tube 1 with the closure plug or stopper 21; when using a low-viscosity suspension, cooling the outer casing of the container to cause the suspension to solidify, while at the same time, due to the prestressing effect, producing a metallic sealing action at the opening 31, by the pressure applied by the plug or stopper 21 to the tube 1, between the two components.

2. Irradiation of the container 17 with the tube 1 therein, in a neutron field, to activate the sample 18 which is serving as a marking substance.

3. Introducing the tube 1 into the housing 2:

(a) When using coal powder:

When the wax closure members 19 and 20 are employed, there is no need for cooling (for example with dry ice); opening of the plug or stopper 21; pushing the tube 17 with its content out of the container 1 by means of the plug or stopper 24 using a suitable, tool (not shown) through the end opening 31 of the container 17; inserting the tube 1 with its discharge opening 4 leading into the housing 2 of the injection apparatus by means of a pair of pliers or the like with the high-pressure closure arrangement 10 in an open condition, through the opening 6 and into the upper or forward portion 7 of the space 8 within the apparatus; and fixing the tube 1 in the housing 2 by a clamping ring 9.

(b) When using coal-oil suspension:

The steps of: introducing the container 17 with tube 1 into a dismantling apparatus (not shown); cooling the content of the tube 1 by surface contact with a cooling jacket whereby the suspension representing the sample solidifies; dismantling the container 17; and introducing the tube.

4. Preparing for and carrying out the injection operation:

The steps of: opening the feed line for the injection agent which is to be introduced through the port 14 and applying a preliminary pressure of the order of magnitude of 20 bars by means of the injection agent in the space 8 within the housing; heating the injection apparatus 2 by heating means 33; after the closure plugs or stoppers 19 and 20 have melted, increasing the pressure of the injection agent by way of the connecting line and the port 14 in the space 8 within the housing to a pressure which is higher than the pressure in the reactor 25; opening the connecting valve 35; and injecting the substance 18 by means of the injection agent which flows through the tube 1.

When using a coal-oil suspension which has set within the tube 1, the heating means 33 causes that suspension to melt, instead of the closure plugs or stoppers 19 and 20. In other respects the manner of performing the injection operation corresponds to the manner of performance when using coal powder.

When injecting a gas, the mode of operation may be the same as when injecting a powder. In that respect, the tube or sleeve member 1 may also be closed by means of diaphragms instead of the plugs or stoppers 19 and 20. After the tube has been introduced into the housing 2 of the injection apparatus and after closure thereof, the diaphragm can be ruptured by a shock pressure from the port 14 by means of an auxiliary agent, for example an inert oil, whereupon the gas is injected into the reaction vessel or some other piece of apparatus.

It will be seen from the foregoing description that the process and the apparatus described are simple and straightforward, permitting easy handling of the materials involved. The apparatus is of such a nature as to provide for safe and easy handling of the radioactive substance in the environment of a hot reaction vessel which is under a high internal pressure, while also complying with the relevant regulations to be observed in relation to the use of radioactive materials.

Various other modifications and alterations may be made in the above-described process and apparatus without thereby departing from the scope of the invention as defined by the appended claims.

What is claimed is:

1. Apparatus for injecting a radioactive sample of a substance into a pressurized reaction chamber comprising:

a radioactive sample;

a generally tubular first container having first and second open ends, and containing said radio-active sample;

a generally tubular, pressure-resistant second container having first and second ends and first interior space for receiving the first container, the second container including;

a sealable charging opening proximate the second end for inserting the first container into the first interior space;

a second interior space before the first interior space and the charging opening, the second end of the first container being in fluid communication with the second interior space;

an inlet port providing fluid communication into the second interior space from outside said second container;

an injection port proximate the first end of the second container for providing fluid communication between the first container and a reaction chamber; and means for securing the second container to a reaction chamber so that the injection port will be in fluid communication with the reaction chamber.

2. Apparatus according to claim 1 further including means for heating the second container and wherein the radioactive sample is a solid meltable by application of heat to the second container.

3. Apparatus according to claim 1 further including means for heating the second container and seals at the ends of the first container of a material meltable by application of heat to the second container to release the radioactive sample.

4. Apparatus according to claim 1 wherein the first container is secured within the first interior space by means comprising a clamping ring having exterior threads and a bore therethrough for the flow of injection medium from the second interior space to the first container, the second container including interior threads to receive the exterior threads of the clamping ring proximate the first interior space.

5. Apparatus according to claim 1 wherein the first interior space and the first container are generally cylindrical and the first interior space is sized to receive the first container in sealing engagement.

6. Apparatus according to claim 1 in combination with high pressure valve means for controlling fluid communication from the injection port.

* * * * *